United States Patent [19]

Ball et al.

[11] 4,452,907
[45] Jun. 5, 1984

[54] PROCESS FOR THE PRODUCTION OF CRYSTALLINE ALUMINOSILICATES AND THEIR USE AS CATALYSTS AND CATALYST SUPPORTS

[75] Inventors: William J. Ball, Capel; David G. Stewart, Epsom, both of England

[73] Assignee: The British Petroleum Company Limited, London, England

[21] Appl. No.: 454,046

[22] Filed: Dec. 28, 1982

Related U.S. Application Data

[63] Continuation of Ser. No. 212,807, Dec. 4, 1980, abandoned.

[30] Foreign Application Priority Data

Dec. 7, 1979 [GB] United Kingdom ................ 7942350

[51] Int. Cl.³ .................. C01B 33/28; B01J 29/06
[52] U.S. Cl. .................. 502/60; 423/328; 423/329; 423/333; 502/61; 502/74; 502/77; 502/202; 502/214
[58] Field of Search ................ 423/326–333; 502/60, 61, 73, 74, 77, 202, 214

[56] References Cited

U.S. PATENT DOCUMENTS

| | | | |
|---|---|---|---|
| 4,061,724 | 12/1977 | Grose et al. | 423/335 |
| 4,151,189 | 4/1979 | Rubin et al. | 423/329 X |
| 4,175,114 | 11/1979 | Plank et al. | 423/329 |
| 4,242,233 | 12/1980 | Ball et al. | 423/328 |
| 4,257,885 | 3/1981 | Grose et al. | 423/328 X |
| 4,285,919 | 8/1981 | Klotz et al. | 423/277 |

FOREIGN PATENT DOCUMENTS

| | | | |
|---|---|---|---|
| 1553209 | 9/1979 | United Kingdom | 423/329 |
| 2018232 | 10/1979 | United Kingdom | 423/329 |

*Primary Examiner*—Edward J. Meros
*Attorney, Agent, or Firm*—Brooks, Haidt, Haffner & Delahunty

[57] ABSTRACT

Crystalline aluminosilicates having a silica to alumina molar ratio greater than 12 are produced by mixing a source of silica, a source of alumina, a source of alkali metal, water and a source of ammonium ions, e.g. ammonia or an ammonium salt, in the absence of an alcohol or alkylene oxide, in the molar proportions (expressed in the case of the silica and alumina sources in terms of the equivalent moles of the oxide, in the case of the alkali metal source in terms of the equivalent moles of the hydroxide (MOH) and in the case of the source of ammonium ions in terms of free ammonia):

$SiO_2$: $Al_2O_3$ greater than 12:1
MOH: $Al_2O_3$ in the range from 1:1 to 20:1
$SiO_2$: $NH_3$ in the range from 1:1 to 200:1
$H_2O$: MOH in the range from 30:1 to 300:1 and maintaining the composition at elevated temperature, such as 120° to 210° C. for a period such that crystallization occurs, typically greater than 4 hours. The crystalline aluminosilicates so-prepared are useful as catalysts and catalyst supports.

15 Claims, No Drawings

PROCESS FOR THE PRODUCTION OF CRYSTALLINE ALUMINOSILICATES AND THEIR USE AS CATALYSTS AND CATALYST SUPPORTS

This is a continuation of application Ser. No. 212,807, filed Dec. 4, 1980, now abandoned.

The present invention relates generally to an improved process for the production of crystalline aluminosilicates and to the use of the crystalline aluminosilicates produced thereby as conversion catalysts and catalyst supports.

Crystalline aluminosilicates, both natural and synthetic, have been shown to contain a wide variety of positive ions. These aluminosilicates have skeletal structures which are made up of three dimensional networks of $SiO_4$ and $AlO_4$ tetrahedra, corner-linked to each other by shared oxygen atoms. There are no unshared oxygen atoms in the anionic framework so that the ratio of the total aluminium and silicon atoms (Al+Si) to oxygen atoms is 1:2 and the negative charges created by the replacement of Si (IV) atoms by Al (III) atoms are neutralised by an electrochemical equivalent of cations. Those cations in the initially formed aluminosilicate are generally alkali metal cations. Until recently it was not possible to synthesise crystalline aluminosilicates having a silica to alumina molar ratio greater than 10:1. However, this has recently been achieved and there has resulted a range of crystalline aluminosilicates having a higher silica to alumina ratio, high stability, extremely high acidity, and the ability to catalyse many kinds of conversion reactions, in particular the conversion of aliphatic compounds into aromatic compounds. This was achieved by the use in the preparation of the aluminosilicate of one or more quaternary alkylammonium compounds such as tetramethylammonium, tetraethylammonium, tetrapropylammonium and tetrabutylammonium compounds. By employing such large cations crystalline aluminosilicates having a silica to alumina ratio greater than 100:1 can be produced. However, the use of quaternary alkylammonium compounds is not without its disadvantages, not the least of which is their relatively high cost. British Patent Specification No.: 1,365,318 discloses an attempt to overcome this disadvantage by employing in the synthesis the precursors of the tetralkylammonium compound, i.e. $R_1R_2R_3N+R_4X$ in which $R_1$, $R_2$ and $R_3$ are selected from aryl, substituted aryl, alkyl, substituted alkyl, cycloalkyl, substituted cycloalkyl and hydrogen, $R_4$ is alkyl, substituted alkyl, cycloalkyl, substituted cycloalkyl, aryl and substituted aryl and X is an electronegative group. In a special embodiment of the invention the compound $R_1R_2R_3N$ may be used in the absence of $R_4X$ provided that the compound $R_1R_2R_4N$ is used. This method only partially alleviates the expense problem and does not eliminate a further disadvantage associated with crystalline aluminosilicates prepared from tetraalkylammonium compounds, namely that in order to exchange an ammonium or other cation into the zeolite preliminary to producing the active form of the catalyst it is necessary to calcine the zeolite.

Recent attempts to overcome the aforesaid disadvantages are described in British Patent Specification No.: 1,553,209 and U.K. Patent Application No.: 2,018,232A. British Patent Specification No.: 1,553,209 describes a method of making such a zeolite by reacting an aqueous mixture comprising at least one silica source, at least one alumina source, at least one alkali not including ammonium or phosphonium compounds, and at least one alcohol, the mixture having the composition:

$SiO_2/Al_2O_3$: 20 to 200
$OH(R)/Al_2O_3$: 0.02 to 0.25
$M_2O/SiO_2$: 10 to 1000
$H_2O/M_2O$: 1 to 100 where M is one or more of lithium, sodium or potassium;

$M_2O$ refers to free alkali; and

OH(R) is a hydroxy group present as an alcohol.

G.B. Patent Application No.: 2,018,232 describes and claims a process for the preparation of crystalline aluminosilicate zeolites having a $SiO_2/Al_2O_3$ molar ratio of at least 12 and a constraint index between 1 and 12, characterised in that an aqueous mixture containing the following compounds:

one or more compounds of an alkali and/or alkaline earth metal, (M),
one or more Al compounds,
one or more Si-compounds,
one or more alcohols (ROH), and
ammonia, in which mixture the various compounds are present in the following molar ratios expressed—with the exception of the alcohols and ammonia—in moles of the oxides:

$SiO_2:Al_2O_3 \geq 12:1$
$(M)_{2/n}O:SiO_2 = 0.01-1.0$
$H_2O:(M)_{2/n}O = 10-500$
$ROH:Al_2O_3 = 5-500$, and
$ROH:NH_3 > 2$ (n is the valency of M) is maintained at elevated temperature until the zeolite has been formed and in that subsequently the crystals of the zeolite are separated from the mother liquor.

Our own published European Application Nos.: 78300773.5 (BP Case 4509) and 78300774.3 (BP Case 4509/4625) describe the use of mono-, di- and trialkanolamines as organic nitrogen bases in the production of crystalline aluminosilicates. A particular advantage of their use is that the precursors of such alkanolamines in the form of an alkylene oxide and ammonia may be used in place of the preformed alkanolamine, thereby reducing the cost relative to quaternary alkylammonium compounds significantly.

We have now unexpectedly found that crystalline aluminosilicates having a silica to alumina molar ratio greater than 12:1 can be produced from an ammonia-containing mixture in the absence of an alcohol or an alkylene oxide. Crystalline aluminosilicates so-produced do not require calcination prior to ion-exchange.

Accordingly, the present invention provides a process for the production of a crystalline aluminosilicate having a silica to alumina molar ratio greater than 12:1 by mixing a source of silica, a source of alumina, a source of alkali metal, water and a source of ammonium ions, and maintaining the mixture at elevated temperature for a time such that crystallisation occurs characterised in that a source of ammonium ions is employed in the absence of an alcohol or alkylene oxide and the source of silica, the source of alumina, the source of alkali metal, water and the source of ammonium ions are mixed in the molar proportions (expressed in the case of the silica and alumina sources in terms of the equivalent moles of the oxide, in the case of the alkali metal source in terms of the equivalent moles of the hydroxide

[MOH] and in the case of the source of ammonium ions in terms of free ammonia):

$SiO_2:Al_2O_3$ 12:1
$MOH:Al_2O_3$ in the range from 1:1 to 20:1
$SiO_2:NH_3$ in the range from 1:1 to 200:1, and
$H_2O:MOH$ in the range from 30:1 to 300:1.

Suitable sources of silica include, for example, sodium silicate, silica hydrosol, silica gel, silica sol and silicic acid. The preferred source of silica is an aqueous colloidal dispersion of silica particles. A suitable commercially available source of silica is LUDOX Colloidal Silica manufactured by Du Pont (LUDOX is a Registered Trade Mark).

Suitable sources of alkali metal include alkali metal hydroxides and alkali metal oxides. Preferably the alkali metal is sodium.

The source of ammonium ions may be for example ammonium hydroxide or an ammonium salt such as the halide, nitrate, sulphate or carbonate. Ammonium hydroxide may be added as an aqueous solution or formed 'in situ' by passing ammonia gas into the aqueous mixture. 35% w/w and 25% w/w aqueous ammonia solutions having densities of 0.880 g/ml and 0.910 g/ml respectively at 20° C. are commercially available and may be used in the process of the invention, but aqueous solutions of other concentrations may also be used.

It will be appreciated that each source of silica, alumina, alkali metal and ammonium ion can be supplied by one or more initial reactants and then mixed together in any order. For example, sodium silicate is a source of both sodium and silica and an aluminosilicate is a source of both alumina and silica. Thus the source of alumina and the source of silica may be supplied in whole or in part by an aluminosilicate, which may be either crystalline or amorphous. A seed, that is a small portion of the desired crystalline product, may be introduced if so desired but it is an advantage of the present invention that the introduction of a seed is not necessary for the efficient performance of the invention.

The molar composition of the initial mixture is preferably as follows:

$SiO_2:Al_2O_3$ in the range from 20:1 to 50:1
$MOH:Al_2O_3$ in the range from 2:1 to 10:1
$SiO_2:NH_3$ in the range from 20:1 to 100:1
$H_2O:MOH$ in the range from 30:1 to 100:1

Even more preferably the molar composition of the initial mixture is as follows:

$SiO_2:Al_2O_3$ in the range from 25:1 to 45:1
$MOH:Al_2O_3$ in the range from 3:1 to 7:1
$SiO_2:NH_3$ in the range from 25:1 to 40:1
$H_2O:MOH$ in the range from 40:1 to 60:1

Conditions which effect the formation of the crystalline aluminosilicate may be, for example, a temperature in the range from 120° to 210° C., preferably from 135° to 190° C. and a pressure in the range from autogenous to 26 bar (400 psig), preferably from autogenous to 16 bar (250 psig). Suitably the pressure may be autogenous, that is the pressure generated within a closed vessel at the crystallisation temperature. Alternatively pressures within the aforesaid ranges above autogenous pressure may be employed. Pressures above autogenous pressure may be achieved for example by pressurising with a suitable gas, e.g. nitrogen. The mixture may suitably be maintained under these conditions for a time of at least 4 hours and preferably from 20 to 150 hours. Generally a time of about 48 will be found suitable though times up to and in excess of 7 days may be employed. Of course the time should not be so protracted that the crystalline aluminosilicate produced is converted to quartz.

The reaction is suitably carried out in a closed vessel capable of withstanding the elevated pressures employed during the process. Furthermore the reaction mixture may be agitated during the formation of the aluminosilicate. The solid aluminosilicate so-prepared may be recovered, e.g. by filtration and washed, suitably with water at a temperature in the range, for example, of from 15° to 95° C.

Crystalline aluminosilicates prepared by the process of the present invention may be used as catalysts or as catalyst supports. The crystalline aluminosilicate may be used on its own or admixed with up to 80% by weight of another support material such as silica or alumina.

Crystalline aluminosilicates prepared in the manner of the present invention will invariably contain alkali metals, which are generally undesirable if the aluminosilicate is to be used for catalytic purposes. Thus it is preferred to reduce the alkali metal content of the aluminosilicate to less than 0.2% by weight, or for certain catalytic applications, such as in the dehydrocyclodimerisation of paraffins to less than 0.02% by weight. This may be achieved by subjecting the aluminosilicate to one or more ion exchanges with a solution containing suitable cations. For example, the aluminosilicate may be ion-exchanged with a solution containing ammonium cations and thereafter calcined to produce the active hydrogen-form of the aluminosilicate. Before ion-exchange it may be preferable to treat the aluminosilicate with a solution of an acid, e.g. an aqueous mineral acid.

For catalytic purposes it is preferred to activate the aluminosilicate before use, suitably by heating in air at a temperature in the range 400° to 700° C. for a period of from 2 to 48 hours.

Further there may be incorporated into the crystalline aluminosilicate one or more metals belonging to Groups IB, IIB, IIIA, IVA, VA or VIII of the Periodic Table of the elements as published by the Chemical Rubber Publishing Company. Suitable metals include copper, silver, zinc, gallium, indium, thallium, lead, antimony, bismuth, iron, cobalt, nickel, ruthenium, rhodium, palladium, iridium and platinum. The amount of the metal or metals incorporated may be in the range from 0.1 to 5.0% by weight based on the weight of the aluminosilicate. The metal or metals may suitably be incorporated by impregnation with a suitable compound or compounds. The compounds of the metals used are suitably those compounds which will decompose on heating to form the corresponding oxides and which are soluble in water, e.g. the nitrates or chlorides. The aluminosilicate may thus be impregnated with an aqueous solution of a compound of the desired metal and the impregnated mass thereafter calcined to produce the metal oxide 'in situ' deposited in the interstices of the aluminosilicate structure. Alternatively, or in addition, the metal or metals may be incorporated by ion-exchange. A suitable method for preparing a gallium-exchanged crystalline aluminosilicate catalyst comprises washing the crystalline aluminosilicate with acidified and/or deionised water, calcining the washed product at an elevated temperature, contacting the calcined product with an acid, refluxing the acid-treated product with a solution of a gallium compound to produce a gallium-exchanged aluminosilicate and washing the gallium-exchanged aluminosilicate with water to render it substantially free from any impregnated gallium or gallium compound.

In a further embodiment of the invention the aluminosilicate employed additionally contains one or more non-metallic elements belonging to Groups IIIA and VA of the Periodic Table, especially boron and phosphorus. The non-metallic element may be incorporated into the aluminosilicate by treatment with a suitable compound containing the non-metallic element, e.g. phosphoric acid, trimethylphosphite or phosphorus trichloride, followed by heating. The amount of the non-metallic element present in the impregnated aluminosilicate preferably ranges from 0.1 to 5.0% by weight.

The crystalline aluminosilicates so-prepared, with or without the hereinbefore described treatments and/or modifications, may be used as catalysts in the form of a fixed or a fluidised bed in aromatisation, disproportionation, cracking, alkylation, dehydrocyclodimerisation, oligomerisation, isomerisation and hydrogenation reactions. Additionally the aluminosilicates may be used as catalysts in the dehydration of alcohols and ethers.

The following Examples are given for the purpose of illustrating the invention.

In the Examples reference will be made to Ludox Type LS30 silica sol and Ludox Type AS40 silica sol. Type LS30 silica sol contains sodium ions as the stabilising counter ions and has a titratable alkali content of 0.1% wt/wt calculated as $Na_2O$. Type AS40 silica sol contains ammonium ions as the stabilising counter ions and has a silica to ammonia ratio (i.e. $SiO_2:NH_3$) of 80:1 molar.

EXAMPLE 1

(a) Preparation of crystalline aluminosilicate

Alumina, Laporte Type A (0.89 g) was dissolved in a solution of sodium hydroxide (1.75 g) in deionised water (12.5 ml) by warming. This solution was then added with vigorous stirring to Ludox Type LS30 silica sol (52.5 g, containing 30% wt/wt silica) and 0.910 aqueous ammonia solution (0.6 ml, containing 25% wt/wt ammonia). The mixture was stirred for three hours and then placed in an agitated, glass-lined pressure vessel and heated at 170° C. for 48 hours. The solid crystalline product was filtered off.

(b) Preparation of active form of crystalline aluminosilicate

The crystalline product recovered from (a) above was ion-exchanged by refluxing with one molar ammonium chloride solution (250 ml). This operation was repeated twice. The mixture was filtered and the solid washed with deionised water (250 ml) and dried at 120° C. for 16 hours. A sample of the solid was calcined by heating at 500° C. and the calcined sample analysed by X-ray fluorescence. It was shown to contain 43% w/w silicon, 1.93% w/w aluminium and less than 0.01% w/w sodium. The analysis corresponds to a silica to alumina molar ratio of 45:1. The X-ray diffraction pattern (XRD) of the calcined crystalline aluminosilicate was determined by standard techniques using as radiation the K-alpha doublet of copper. The pattern expressed in terms of 2-theta, d(Angstroms) and $I/I_o$ is given in Table 1. The XRD pattern is characteristic of an MFI-type zeolite as defined in the Atlas of Zeolite Structure Types by W. M. Meier and D. H. Olson, published by the Structure Commission of the International Zeolite Association, 1978.

10 g of the uncalcined aluminosilicate prepared as described above was crushed to powder and mixed with 10 g Ludox silica sol (containing 30% wt/wt silica). The suspension was evaporated to dryness on a steambath and finally dried at 120° C. The solid was then broken down to form 5 to 16 mesh (BSS) granules and calcined at 500° C. for 16 hours in air.

EXAMPLE 2

(a) Preparation of crystalline aluminosilicate

Alumina, Laporte Type A (13.35 g) was dissolved in a solution of sodium hydroxide (26.25 g) in deionised water (187.5 ml) by warming. This solution was then added with stirring to Ludox silica sol Grade AS40 (590 g, containing 40% wt/wt silica) and 0.910 aqueous ammonia solution (9.0 ml, containing 25% wt/wt ammonia). The pH of the mixture was 13.1

1.5 g of the active form of the crystalline aluminosilicate prepared as described in Example 1 was added and the whole was placed in a rocking stainless steel autoclave and heated at 170° C. for 64 hours. The crystalline aluminosilicate product was filtered off. It had a silica to alumina molar ratio of greater than 12:1 and an X-ray diffraction pattern after calcination, substantially the same as that shown in Table 1.

(b) Preparation of active form of crystalline aluminosilicate

The solid product from (a) was ion-exchanged by refluxing with one molar ammonium chloride solution (500 ml). This operation was repeated twice. The mixture was filtered and the solid washed with deionised water (1000 ml) and dried at 120° C. for 16 hours. The solid was then broken down to form 5 to 16 mesh (BSS) granules and calcined at 500° C. for 16 hours in air.

EXAMPLE 3

8.0 g of the granules of the activated crystalline aluminosilicate prepared as described in Example 1 were mixed with an aqueous gallium nitrate solution (6 ml, containing b 0.05 g gallium/ml) and the whole evaporated to dryness on a steam-bath. The solid was dried at 120° C. for 16 hours and activated by heating in air at 500° C. for 16 hours.

EXAMPLE 4

Alumina, Laporte Type A (0.89 g) was dissolved in a solution of sodium hydroxide (1.75 g) in deionised water (12.5 ml) by warming. This solution was then added with vigorous stirring to a mixture of Ludox silica sol, Type AS40 (39.4 g, containing 40% wt/wt silica) and deionised water (13.1 ml). The suspension was stirred for three hours and then placed in an agitated glass-lined pressure vessel and heated at 170° C. for 64 hours.

The solid product was filtered off. It had a silica to alumina molar ratio of greater than 12:1 and an X-ray diffraction pattern, after calcination, substantially the same as that shown in Table 1. The product was processed as described in Example 1(b).

Testing of Crystalline Aluminosilicate as Catalysts

EXAMPLE 5

The activity of the activated aluminosilicate prepared as described in Example 1 was tested by passing a gaseous feed of methanol over the catalyst in a glass reactor at 400° C. and 3.2 seconds contact time.

Of the methanol fed, 2% (molar) was converted to $C_2$, 27% to $C_3$ and 30% to $C_4$ hydrocarbons and the remainder was a complex mixture of straight- and branched-chain hydrocarbons and aromatics. The methanol conversion was 100%.

EXAMPLE 6

The activity of the activated aluminosilicate prepared as described in Example 1 was tested by passing a gaseous feed of a $C_3$ hydrocarbon mixture (78.1% propane, 19.1% propylene and 2.8% ethane) over the catalyst in a heated glass reactor. The conditions used and the results obtained therefrom are given in the following Table 2.

EXAMPLE 7

The activity of the activated aluminosilicate prepared as described in Example 2 was tested as described in Example 6. The conditions used and the results obtained therefrom are given in the following Table 2.

EXAMPLE 8

The activity of the activated catalyst prepared as described in Example 3 was tested as described in Example 6. The conditions used and the results obtained therefrom are given in the following Table 2.

EXAMPLE 9

The activity of the activated catalyst prepared as described in Example 4 was tested in the manner described in Example 6. The conditions used and the results obtained therefrom are given in the following Table 2.

TABLE 1

| X-Ray Diffraction Data for Aluminosilicates after Calcination at 500° C./for 6 hours. | | |
|---|---|---|
| 2-Theta | d(Angstrom) | $I/I_0$ |
| 4.96 | 17.823 | 4 |
| 5.11 | 17.312 | 5 |
| 5.14 | 17.181 | 5 |
| 7.09 | 12.462 | 6 |
| 7.96 | 11.104 | 100 |
| 8.87 | 9.973 | 55 |
| 9.11 | 9.713 | 17 |
| 11.94 | 7.416 | 5 |
| 13.23 | 6.693 | 7 |
| 13.96 | 6.344 | 11 |
| 14.83 | 5.976 | 14 |
| 15.56 | 5.695 | 10 |
| 15.94 | 5.560 | 12 |
| 16.67 | 5.319 | 5 |
| 17.70 | 5.013 | 5 |
| 17.85 | 4.971 | 6 |
| 19.29 | 4.603 | 6 |
| 20.38 | 4.358 | 9 |
| 20.89 | 4.253 | 11 |
| 22.25 | 3.996 | 6 |
| 23.14 | 3.844 | 89 |
| 23.35 | 3.811 | 64 |
| 23.79 | 3.741 | 34 |
| 23.95 | 3.716 | 42 |
| 24.45 | 3.641 | 29 |
| 24.81 | 3.590 | 4 |
| 25.64 | 3.475 | 8 |
| 25.94 | 3.435 | 13 |
| 26.28 | 3.391 | 11 |
| 26.67 | 3.343 | 9 |
| 26.97 | 3.307 | 10 |
| 27.44 | 3.251 | 4 |
| 29.33 | 3.046 | 10 |
| 29.96 | 2.983 | 11 |
| 30.08 | 2.971 | 11 |
| 30.39 | 2.941 | 6 |
| 32.80 | 2.731 | 4 |

TABLE 2

| Test | Hours on stream | Reaction temperature °C. | Contact time sec | $C_3^2$ Conversion % | Molar Yields[3] % | | | | Selectivity to Aromatics | Composition of aromatics % | | |
|---|---|---|---|---|---|---|---|---|---|---|---|---|
| | | | | | $CH_4$ | $C_2H_4$ | $C_2H_6$ | Aromatics | | Benzene | Toluene | Xylene |
| Ex 6 | 2 | 450 | 16.5 | 22.7 | 5.5 | 0.7 | 4.6 | 11.9 | 52.4 | 17 | 37 | 21 |
| | 2 | 500 | 16.6 | 57.9 | 13.4 | 1.4 | 11.4 | 31.2 | 53.9 | 26 | 42 | 19 |
| | 2 | 550 | 16.3 | 85.3 | 20.5 | 3.1 | 11.0 | 50.7 | 59.4 | 33 | 37 | 12 |
| | 2 | 550 | 6.2 | 52.2 | 13.6 | 5.0 | 9.2 | 24.4 | 46.7 | 21 | 42 | 21 |
| Ex 7 | 2 | 450 | 16.9 | 19.5 | 2.4 | 0.5 | 2.4 | 16.6 | 85.1 | 19 | 47 | 30 |
| | 2 | 500 | 17.6 | 35.5 | 8.6 | 1.3 | 7.4 | 18.2 | 51.3 | 18 | 35 | 20 |
| | 2 | 550 | 17.1 | 67.8 | 17.0 | 3.2 | 10.4 | 37.2 | 54.9 | 24 | 39 | 7 |
| | 2 | 550 | 5.9 | 30.1 | 9.3 | 4.8 | 6.4 | 9.6 | 31.9 | 19 | 41 | 27 |
| Ex 8 | 1 | 550 | 18.0 | 95.4 | 13.6 | 0.7 | 11.0 | 70.2 | 73.6 | 34 | 34 | 0 |
| | 1 | 550 | 6.1 | 67.6 | 8.6 | 0.1 | 5.2 | 51.7 | 76.5 | 32 | 44 | .5 |
| Ex 9 | 1 | 550 | 18.0 | 86.9 | 16.3 | 2.5 | 8.6 | 59.7 | 68.7 | 30 | 38 | .4 |

In the above Examples and Table 2.

1. Contact time $= \dfrac{\text{Volume of catalyst in mls}}{\text{Total volume of gas (in mls/sec at } NTP)}$ 2. $C_3$ Conversion $= \dfrac{\text{Moles of } C_3 \text{ hydrocarbon consumed}}{\text{Moles of } C_3 \text{ hydrocarbon fed}} \times 100$ 3. Molar Yield $= \dfrac{\text{Moles of } C_3 \text{ hydrocarbon converted to particular product}}{\text{Moles of } C_3 \text{ hydrocarbon fed}} \times 100$ 4. Selectivity $= \dfrac{\text{Moles of } C_3 \text{ hydrocarbon converted to aromatics}}{\text{Moles of } C_3 \text{ hydrocarbon consumed}} \times 100$

We claim:

1. A process for the production of a crystalline aluminosilicate having a silicon to alumina molar ratio greater than 12:1 by mixing a source of silica, a source of alumina, a source of alkali metal, water and an inorganic source of ammonium ions, maintaining the mixture at elevated temperature for a period such that crystallisation occurs characterized in that the source of ammonium ions is employed in the absence of an alcohol or any "seed", i.e., a small portion of the crystalline aluminosilicate desired, or alkylene oxide and the source of silica, the source of alumina, the source of alkali metal, water and the source of ammonium ions are mixed in the molar proportions (expressed in the case of the silica and alumina sources in terms of the equivalent moles of the oxide, in the case of the alkali metal source in terms of the equivalent moles of the hydroxide (MOH) and in the case of the source of ammonium ions in terms of free ammonia):

SiO$_2$:Al$_2$O$_3$ greater than 12:1
MOH:Al$_2$O$_3$ in the range from 1:1 to 20:1
SiO$_2$:NH$_3$ in the range from 1:1 to 200:1, and
H$_2$O:MOH in the range from 30:1 to 300:1.

2. A process according to claim 1 wherein the source of ammonium ions is ammonium hydroxide.

3. A process according to claim 2 wherein the ammonium hydroxide is added as an aqueous solution.

4. A process according to claim 2 wherein the ammonium hydroxide is formed 'in situ' by passing ammonia gas into the aqueous mixture.

5. A process according to claim 1 wherein the source of ammonium ions is an ammonium salt.

6. A process according to any one of the preceding claims wherein the molar composition of the initial mixture is:

SiO$_2$:Al$_2$O$_3$ in the range from 20:1 to 50:1
MOH:Al$_2$O$_3$ in the range from 2:1 to 10:1
SiO$_2$:NH$_3$ in the range from 20:1 to 100:1
H$_2$O:MOH in the range from 30:1 to 100:1.

7. A process according to claim 7 wherein the molar composition of the initial mixture is:

SiO$_2$:Al$_2$O$_3$ in the range from 25:1 to 45:1
MOH:Al$_2$O$_3$ in the range from 3:1 to 7:1
SiO$_2$:NH$_3$ in the range from 25:1 to 40:1
H$_2$O:MOH in the range from 40:1 to 60:1.

8. A process according to claim 1 wherein the temperature is in the range from 120° to 210° C.

9. A process according to claim 1 wherein, the alkali metal content of the crystalline aluminosilicate is reduced to less than 0.2% by weight.

10. A process according to claim 9 wherein the alkali metal content is reduced by ion-exchange with a solution containing ammonium cations followed by calcination to produce the active hydrogen-form of the aluminosilicate.

11. A process according to claim 1 wherein, there is incorporated into the crystalline aluminosilicate one or more of the metals copper, silver, zinc, gallium, indium, thallium, lead, antimony, bismuth, iron, cobalt, nickel, ruthenium, rhodium, palladium, iridium and platinum.

12. A process according to claim 11 wherein the metal is gallium.

13. A process according to claim 11 wherein the metal or metals is incorporated by impregnation.

14. A process according to claim 11 wherein the metal or metals is incorporated by ion-exchange.

15. A process according to claim 1 wherein, prior to the use, there is incorporated into the crystalline aluminosilicate either boron or phosphorus.

* * * * *

UNITED STATES PATENT AND TRADEMARK OFFICE
CERTIFICATE OF CORRECTION

PATENT NO. : 4,452,907
DATED      : June 5, 1984
INVENTOR(S) : WILLIAM J. BALL et al It is certified that error appears in the above-identified patent and that said Letters Patent is hereby corrected as shown below:

Col. 6, line 39, After word "containing" letter --b-- should be omitted.

Col. 3, line 66, After "48" word --hours-- has been omitted

IN THE CLAIMS:

Claim 1, col. 8, line 54, "silicon" should read --silica--

Claim 7, col 9, line 24, "according to claim 7" should read --according to claim 6--

Signed and Sealed this

Nineteenth Day of March 1985

[SEAL]

Attest:

DONALD J. QUIGG

Attesting Officer    Acting Commissioner of Patents and Trademarks